United States Patent [19]

Collins et al.

[11] 4,154,761
[45] May 15, 1979

[54] PHARMACOLOGICALLY ACTIVE COMPOUNDS

[75] Inventors: Ian Collins, Ware, England; Philip D. Wicks, Forfar, Scotland

[73] Assignee: Allen & Hanburys Limited, London, England

[21] Appl. No.: 763,618

[22] Filed: Jan. 28, 1977

[30] Foreign Application Priority Data

Feb. 9, 1976 [GB] United Kingdom ............. 4929/76
Aug. 24, 1976 [GB] United Kingdom ........... 35182/76

[51] Int. Cl.² ........................................... C07C 91/06
[52] U.S. Cl. ..................... 260/570.5 P; 260/340.5 R; 260/501.18; 260/558 A; 260/559 A; 260/562 P; 260/566 D; 260/566 F; 260/570.5 C; 260/570.6; 260/574; 260/577; 424/282; 424/316; 424/324; 424/330; 560/19; 560/132
[58] Field of Search ........... 260/570.6, 501.17, 501.18, 260/570.5 P

[56] References Cited

U.S. PATENT DOCUMENTS

| | | | |
|---|---|---|---|
| 3,300,532 | 1/1967 | Zellner | 260/570.5 |
| 3,536,712 | 10/1970 | Keck et al. | 260/570.6 X |
| 3,644,353 | 2/1972 | Lunts et al. | 260/570.6 X |
| 3,816,516 | 6/1974 | Cox et al. | 260/501.17 |
| 4,021,485 | 5/1977 | Schromm et al. | 260/570.6 |

FOREIGN PATENT DOCUMENTS

1458251 12/1976 United Kingdom ............. 260/570.6

*Primary Examiner*—Robert V. Hines
*Attorney, Agent, or Firm*—Bacon & Thomas

[57] ABSTRACT

Compounds of the general formula (I):

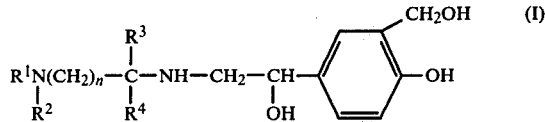

in which $R^1$ represents hydrogen or a straight or branched chain alkyl group, or an acyl group of the formula $-COR^5$ (in which $R^5$ represents a hydrogen atom or a straight or branched chain alkyl group);

$R^2$ represents an aryl group of the formula:

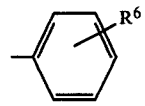

(in which $R^6$ represents a hydrogen atom or independently one or more of the following groups, that is, hydroxy, alkoxy, alkyl, halogen, dialkylamino and trifluoromethyl, or may represent a 3,4-methylenedioxy group

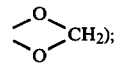

$R^3$ and $R^4$ may independently represent hydrogen or a straight or branched chain alkyl group; and n represents 1, 2 or 3; and pharmaceutically acceptable salts thereof; and hydrates of said compounds or salts thereof. The invention also includes processes for the production of these compounds, compositions containing them and methods of treatment using them.

23 Claims, No Drawings

PHARMACOLOGICALLY ACTIVE COMPOUNDS

This invention relates to new compounds having a stimulant action on β-adrenoreceptors, and to processes for their production as well as pharmaceutical compositions containing them and to methods of treatment utilising them.

According to the invention there are provided novel $\beta_2$-adrenoreceptor stimulants of the general formula (I):

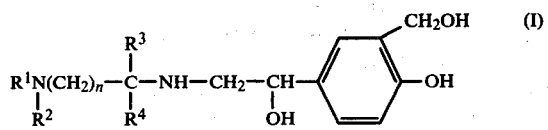

in which $R^1$ represents hydrogen or a straight or branched chain alkyl group or an acyl group of the formula $COR^5$ (in which $R^5$ represents a hydrogen atom or a straight or branched chain alkyl group);

$R^2$ represents an aryl group of the formula:

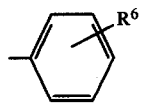

(in which $R^6$ represents a hydrogen atom or independently one or more of the following groups, that is, hydroxy, alkoxy, alkyl, halogen, dialkylamino and trifluoromethyl, or may represent a 3,4-methylenedioxy group

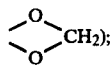

$R^3$ and $R^4$ may independently represent hydrogen or a straight or branched chain alkyl group;

n represents 1, 2 or 3.

The terms "alkyl" and "alkoxy" when used above as a whole or part of a group contain 1 to 6 carbon atoms, particularly 1 to 4 carbon atoms.

In a preferred group of compounds $R^1$ represents hydrogen, methyl, ethyl, or acetyl; $R^2$ represents phenyl, p-methoxyphenyl, p-fluorophenyl, o- or p-tolyl, p-hydroxyphenyl or methylene dioxyphenyl; $R^3$ represents hydrogen or in particular methyl, $R^4$ represents hydrogen or in particular methyl.

In a particularly preferred group of compounds $R^1$ represents hydrogen, methyl, ethyl or acetyl, $R^2$ represents phenyl or o- or p-tolyl, $R^3$ represents methyl, $R^4$ represents hydrogen or methyl.

Particularly preferred compounds are 4-hydroxy-$\alpha^1$-[[[1-methyl-3-(methylphenylamino)propyl]amino]methyl]-1,3-benzenedimethanol, dihydrochloride, hydrate and 4-hydroxy-$\alpha^1$-[[[1-methyl-2-(methylphenylamino)ethyl]amino]methyl]-1,3-benzenedimethanol.

The compounds according to the invention have, in general, a selective stimulant effect on $\beta_2$-adrenergic receptors, so that they can be used as bronchodilators without producing a significant increase in the heart rate. Like known $\beta_2$-selective stimulants the compounds are also effective as inhibitors of gastric acid secretion and as relaxants of uterine muscle for the prevention of premature labour.

Some of the compounds of formula (I) as well as their pharmaceutically acceptable salts differ from known selective $\beta_2$-adrenoreceptor stimulants in that they are more active on respiratory smooth muscle than on skeletal muscle, and thus they act as bronchodilators at doses that minimise the undesired effects of tremor which may occur with known selective $\beta_2$-adrenoreceptor stimulants. The compounds are particularly useful in the treatment of bronchospasm.

The $\beta_2$-stimulant activity was demonstrated by an ability of the compounds to induce relaxation of the spontaneous tone of the guinea pig isolated trachea with accompanying minimal effect on the guinea pig isolated atrium.

The relative selectivity of action of the compounds of formula (I) on respiratory smooth muscle as opposed to skeletal muscle is clearly demonstrated in the anaesthetised cat. The compound is injected through a cannulated jugular vein in an anaesthetised cat which has undergone a bilateral vagotomy. The effects on respiratory smooth muscle, skeletal muscle, blood pressure and heart rate are measured simultaneously. The bronchodilator activity on respiratory smooth muscle was assessed by measuring the effects of the compounds in preventing increases in airways pressure induced by 5-hydroxytryptamine. Airways pressure was measured using a modification of the Dixon and Brodie technique (J. Physiology, 31, 97-173, 1903). The β-stimulant activity on skeletal muscle was assessed by determining the effects of the compounds in decreasing tension of the left soleus muscle developed during a sub-maximal tetanus. The procedure is described by Bowman and Nott, Br. J. Pharmac., 38, 37-49, 1970. Blood pressure was monitored from a common carotid artery and the heart rate measured by an instantaneous ratemeter triggered by the pulse pressure.

(−) Isoprenaline was used as the reference compound in all the experiments.

A further useful activity which has been noted with some of the compounds according to the invention is that they have a reduced effect on the blood pressure, so that incidence of reflex tachycardia may be reduced in conscious animals in which barostatic reflexes are unimpaired.

As the compounds of general formula (I) possess at least one asymmetric carbon atom, the invention also includes all the possible optically active forms and racemic mixtures of the compounds. Mixtures of racemic compounds may be separated by fractional crystallisation of the bases or their acid addition salts and each racemate may then be resolved by conventional methods, for example by salt formation with an optically active acid, followed by fractional crystallisation.

The invention also extends to pharmaceutically acceptable salts and hydrates of the compounds of formula (I). Such salts include acid addition salts, for example salts with inorganic acids, such as hydrochlorides and sulphates and salts with organic acids, such as acetates. Advantage may also be taken of the amphoteric nature of the compounds to form salts with alkali metals e.g. sodium salts.

The compounds of formula (I) may be prepared by a number of processes and examples of such processes are given below. (1) The compounds of formula (I) above may be prepared by reducing compounds of formula (II):

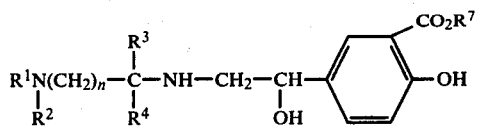

in which $R^1$, $R^2$, $R^3$, $R^4$ and n have the meanings given above and $R^7$ represents an alkyl group containing 1 to 4 carbon atoms, with a reducing agent, such as a complex metal hydride, for example lithium aluminium hydride in an aprotic solvent, such as an ether, for example diethyl ether, dioxan, tetrahydrofuran or diglyme. Alternatively, compounds of formula (I) may be prepared by reduction of the esters (II) with reagents such as sodium dihydrobis-(2-methoxyethoxy) aluminate in an aprotic solvent, such as tetrahydrofuran, or a hydrocarbon such as benzene, or with calcium or sodium borohydride in a suitable solvent, such as a lower alkanol, for example ethanol. Compounds of formula (II) may themselves be prepared from compounds of formula (III):

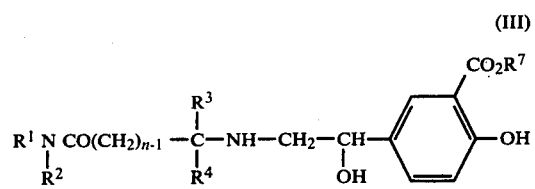

by the action of a reducing agent such as diborane.

The compounds of formula (II) or (III) above, where $R^4$ is hydrogen, may be prepared by reductive alkylation of an amine of formula (V) with a ketone or aldehyde of formula (IV):

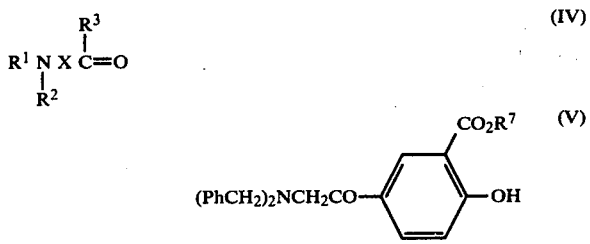

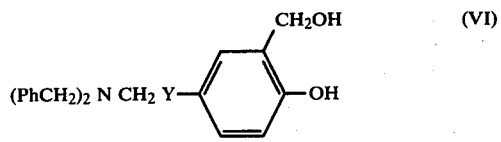

in which $R^1$, $R^2$, $R^3$, $R^7$ and n have the meanings given above and X represents —$(CH_2)_n$— or —$CO(CH_2)_{n-1}$, with hydrogen in the presence of a catalyst, for example a noble metal catalyst, such as palladium, platinum or mixtures thereof, in the presence of a solvent, such as an alkanol, preferably ethanol. (2) The compounds of formula (I) may also be prepared by reductive alkylation of an amine of formula (VI):

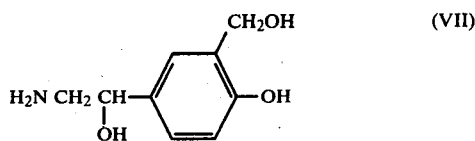

in which Y represents —CHOH or C=O, with a ketone or aldehyde of formula (IV), in which $R^1$, $R^2$ and $R^3$ have the meanings defined above, and X represents $(CH_2)_n$ with hydrogen in the presence of a catalyst, for example a noble metal catalyst, such as palladium and platinum or mixtures thereof, in a solvent, such as an alkanol, preferably ethanol. (3) The compounds of formula (I) may also be prepared by reductive alkylation of an amine of formula (VII):

with a ketone or aldehyde of formula (IV) wherein X represents $(CH_2)_n$ by (a) a catalytic hydrogenation procedure as described in (1) or (2) or by (b) use of a reducing agent such as a complex metal hydride, in particular sodium or potassium borohydride or sodium cyanoborohydride, in a solvent such as an alkanol, preferably methanol or ethanol. The process (a) is related to that of (2) above since the compound of formula (VII) may be prepared by the debenzylation of the compound of formula (VI) for example with hydrogen in the presence of a noble metal catalyst. In processes (a) and (b) the phenolic groups in compounds (VI) and (VII) may be protected for example as esters such as an acetate, which may be subsequently removed by hydrolysis with acid or alkali, or as ethers such as methyl or benzyl ether, which group may be subsequently removed by treatment with, for example, mineral acid such as hydrobromic acid. If a benzyl ether is chosen as the protecting group, then in process (a) the group will be removed during the hydrogenation step. In process (b) the benzyl group will be removed subsequently by catalytic hydrogenation or by mineral acid such as hydrobromic acid. (4) The compounds of formula (I) may also be prepared by condensing an amine of formula (VIII) with a glyoxal of formula (IX):

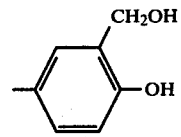

AR CO CHO    (IX)

in which $R^1$, $R^2$, $R^3$, $R^4$ and n have the meanings given above and Ar represents the group

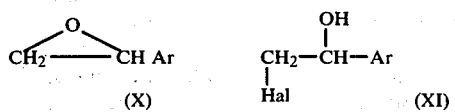

or a group convertible thereto. The so-formed Schiff's base is then reduced with a reducing agent such as a complex metal hydride, for example, lithium aluminium hydride, in a suitable solvent or in the presence of hydrogen and a catalyst, for example a noble metal catalyst, such as palladium, platinum or mixtures thereof, in a solvent, such as an alkanol preferably ethanol. (5) The compounds of formula (I) may also be prepared by reacting an amine of formula (VIII) with an epoxide of formula (X) or a halohydrin of formula (XI):

$$\underset{(X)}{CH_2 \overset{O}{-\!\!\!-\!\!\!-} CH\ Ar} \qquad \underset{Hal\quad (XI)}{\overset{OH}{\underset{|}{CH_2-CH-Ar}}}$$

in which Ar has the meaning given above and Hal represents a halogen atom, in a solvent such as a hydrocarbon, for example toluene, or an alkanol, such as ethanol.

One may also utilize an epoxide in which the group Ar represents a group convertible to a group

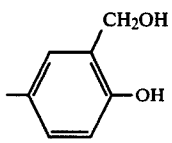

An example of such a group is

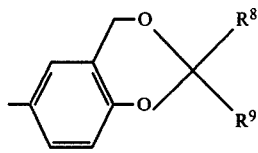

in which $R^8$ and $R^9$ are the same or different and are straight or branched chain alkyl groups or together form a methylene group —$(CH_2)_m$— wherein m is 3, 4 or 5. This group may be hydrolysed to form the group

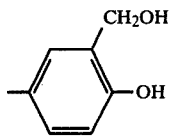

(6) The compounds of the invention where $R^4$ is hydrogen may also be prepared by the hydrogenation of the benzyl derivative of formula (XII):

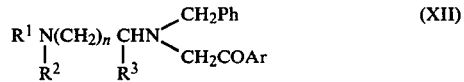

in which $R^1$, $R^2$, $R^3$, n and Ar have the meanings given in the presence of a catalyst for example a noble metal catalyst, such as platinum, palladium or mixtures thereof, in a solvent such as an alkanol, for example ethanol.

The compounds of formula (XII) may be prepared by the condensation of the N-benzylamine of formula (XIII) with a halo ketone of formula (XIV):

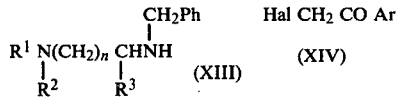

in which $R^1$, $R^2$, $R^3$, n, Hal and Ar have the meanings given above, in a solvent such as a hydrocarbon, for example toluene, a ketone, such as methyl ethyl ketone, an alkanol, such as ethanol or a halogenated hydrocarbon, such as chloroform. (7) In another process one may reduce an intermediate of the formula (XV):

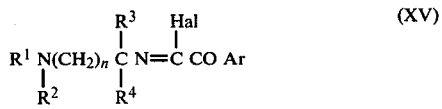

in which $R^1$, $R^2$, $R^3$, $R^4$, n, Hal and Ar have the above stated meanings. This reduction may be effected with diborane, lithium aluminium hydride or an alkali metal hydride. The compound of formula (XV) may be prepared by the condensation of a benzoyl halide with an appropriate isocyanide. (8) The compounds of formula (I), except where $R^6$ represents OH may also be prepared by hydroxymethylation of a compound of formula (XVI):

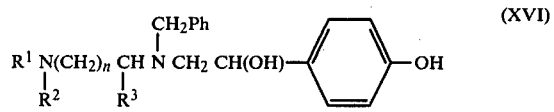

in which $R^1$, $R^2$, $R^3$ and n have the meanings defined above, with formaldehyde or a formaldehyde yielding compound in the presence of a strong base and an alkali metal borate, followed by catalytic debenzylation.

In carrying out the hydroxymethylation process, formaldehyde itself or any suitable source of formaldehyde such as paraformaldehyde may be used. An aqueous solution of formaldehyde, for example 40% Formalin is preferred. The reaction is carried out in the presence of a strong base, preferably an alkali metal hydroxide such as sodium hydroxide, and an alkali metal borate, in particular sodium borate. The reaction is preferably carried out at ambient temperature.

(9) The compounds of formula (I) where $R^4$ is hydrogen and $R^6$ is not OH may also be prepared by chloromethylation of a compound of formula (XVII):

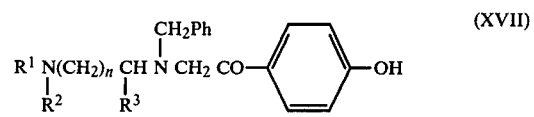

in which $R^1$, $R^2$, $R^3$ and n have the meanings defined above, with formaldehyde and hydrochloric acid, preferably at room temperature. The resultant chloromethyl derivative of formula (XVIII):

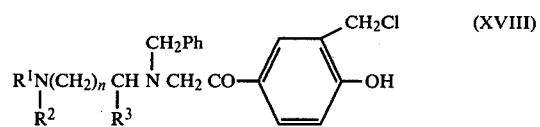

is then hydrolysed with water, preferably with heating, to the hydroxymethyl derivative (XIX):

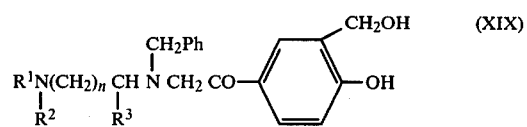

Reduction of this compound with a suitable reducing agent, for example a complex metal hydride, such as sodium borohydride followed by the subsequent removal of the N-benzyl group gives the compound of formula (I).

The amines of formula (VIII) utilised in process (4) may be prepared by the following reaction sequence:

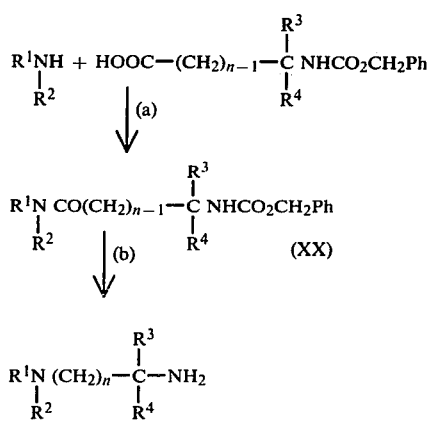

The first step (a) is carried out in the presence of a condensing agent, preferably carbonyl diimidazole or dicyclohexyl carbodiimide, in tetrahydrofuran. The so-formed amide (XX) is hydrogenated in the presence of a noble metal catalyst, preferably palladium on charcoal to remove the benzyloxycarbonyl group followed by reduction with a reducing agent such as diborane in an aprotic solvent, such as tetrahydrofuran.

This route is particularly useful for the preparation of optically active amines, where $R^3$ and $R^4$ are different. The benzyloxycarbonyl group is a preferred protecting group but other suitable protecting groups can be used.

The invention also provides pharmaceutical compositions which are characterised in that they contain a compound according to the invention, preferably in association with a pharmaceutically acceptable carrier or diluent. The compositions may include, for example, solid or liquid preparations for oral use, or may be in the form of suppositories, injections or in a form suitable for administration by inhalation.

Oral administration is most convenient in the form of tablets which may be prepared according to conventional methods, and may be coated if required. Soluble tablets suitable for sublingual administration may also be used.

Injections may be formulated with the aid of physiologically acceptable carriers and agents as solutions, suspensions or as dry products for reconstitution before use.

For administration by inhalation the compositions according to the invention can be in the form of a metered dose inhalation aerosol, a solution or suspension suitable for nebulisation by mechanical means or as a cartridge from which the powdered composition may be inhaled with the aid of a suitable device.

The dosage at which the active ingredients are administered may vary within a wide range. A suitable per diem dosage range for systemic use is generally from 0.5 to 100 mg. The pharmaceutical compositions may with advantage be formulated to provide a dose within this range either as a single unit or a number of units.

In the use of an aerosol for bronchodilatation the dosage unit may be determined by providing a metering valve in the aerosol pack so that it delivers a metered amount on use. Such a metered amount may be of the order of 10–1000 μg.

The following Examples illustrate the invention.

EXAMPLE 1

4-Hydroxy-$\alpha^1$-[[[1-methyl-2-(methylphenylamino)ethyl]amino]methyl]-1,3-benzenedimethanol (a)

2-Hydroxy-5-[1-hydroxy-2-[[1-methyl-2-(methylphenylamino)ethyl]amino]ethyl]benzoic acid, methyl ester, dihydrochloride 2-Hydroxy-5-[[bis(phenylmethyl)amino]acetyl]benzoic acid, methyl ester was generated from the hydrochloride salt (10.44 g) with 8% sodium bicarbonate and extracted into ethyl acetate. A solution of the free base and 1-(N-methyl-N-phenylamino)-2-propanone (4.0 g) in ethanol (400 ml) was hydrogenated at room temperature and atmospheric pressure over pre-reduced 10% palladium oxide on charcoal (2.0 g) and 5% platinum oxide on charcoal (2.0 g). Hydrogen uptake was complete in 72 hours.

The catalysts were filtered off, the solvent was removed in vacuo and the residue was dissolved in dry ether. The solution was filtered and treated with ethereal hydrogen chloride to give the product as an off-white solid (9.3 g).

Recrystallisation from ethyl acetate and light petroleum gave an off-white powder, m.p. 155°–160°.

(b)

4-Hydroxy-$\alpha^1$-[[[1-methyl-2-(methylphenylamino)ethyl]amino]methyl]-1,3-benzenedimethanol 2-Hydroxy-5-[1-hydroxy-2-[[1-methyl-2-(methylphenylamino)ethyl]amino]ethyl]benzoic acid, methyl ester was generated from the dihydrochloride salt (3.5 g) with sodium bicarbonate and extracted into ethyl acetate. A solution of the free base in tetrahydrofuran (20 ml) was added dropwise to lithium aluminium hydride (1.0 g) in tetrahydrofuran (100 ml) at 0°. The mixture was then stirred overnight at room temperature.

Water (5 ml) was added cautiously followed by 5 M hydrochloric acid (ca. 30 ml) until the suspension had dissolved. The stirred mixture was adjusted to pH 9 with sodium bicarbonate and the suspension was filtered. The filtrate was evaporated in vacuo and the residue was partitioned between sodium bicarbonate and ethyl acetate. The organic layer was dried ($MgSO_4$) and evaporated in vacuo. The residue was stirred with dry ether and the liquors were decanted from the remaining gum and left to stand. The product crystallised as a white powder (700 mg), m.p. 102°–107°. Found: C, 69.2; H, 7.9; N, 8.7 $C_{19}H_{26}N_2O_3$ requires C, 69.1; H, 7.9; N, 8.5%.

EXAMPLE 2

N-[2-[[2-Hydroxy-2-[4-hydroxy-3-(hydroxymethyl)phenyl]ethyl]amino]-2-methylethyl]-N-phenylacetamide A solution of N-(2-oxopropyl)-N-phenylacetamide (3 g) and 4-hydroxy-$\alpha^1$-[[bis(phenylmethyl)amino]methyl]-1,3-benzenedimethanol (5.7 g) in ethanol (400 ml) was hydrogenated at room temperature and atmospheric pressure over 10% palladium oxide on charcoal (2 g) and 5% platinum oxide on charcoal (2.0 g). Hydrogen uptake as complete in 48 hours.

The catalysts were filtered off and the solvent was evaporated in vacuo to give a yellow gum which was triturated with dry ether to yield a buff powder (2.1 g) m.p. 120°–128° (from ethyl acetate).

EXAMPLE 3

4-Hydroxy-$\alpha^1$-[[[1-methyl-2-(phenylamino)ethyl]amino]methyl]-1,3-benzenedimethanol, dihydrochloride A solution of 1-(phenylamino)-2-propanone (1.95 g) and 4-hydroxy-$\alpha^1$-[[bis(phenylmethyl)amino]methyl]-1,3-benzenedimethanol (4.75 g) in ethanol (250 ml) was hydrogenated at room temperature and atmospheric pressure over 10% palladium oxide on charcoal (1.5 g) and 5% platinum oxide on charcoal (1.5 g). Hydrogen uptake was complete after 27.5 hours. The catalysts were filtered off, the solvent was evaporated in vacuo and the residue was dissolved in ethyl acetate. The solution was filtered through Hyflo and treated with ethereal hydrogen chloride. The precipitate was washed with dry ether and the product was obtained as a cream powder (4.6 g) m.p. >200° (dec.).

EXAMPLE 4

4-Hydroxy-$\alpha^1$-[[[1-methyl-3-(phenylamino)propyl]amino]methyl]-1,3-benzenedimethanol, dihydrochloride, hemihydrate (a) 2-Hydroxy-5-[1-hydroxy-2-[[1-methyl-2-[(phenylamino)carbonyl]ethyl]amino]ethyl]benzoic acid, methyl ester 2-Hydroxy-5-[[bis(phenylmethyl)amino]acetyl]benzoic acid, methyl ester was generated from the hydrochloride salt (14.42 g) with 8% sodium bicarbonate and extracted into ethyl acetate. A solution of the free base and acetoacetanilide (6.0 g) in ethanol (400 ml) was hydrogenated at room temperature and atmospheric pressure over pre-reduced 10% palladium oxide on charcoal (2.5 g) and 5% platinum oxide on charcoal (2.5 g) catalysts. Hydrogen uptake was complete in 72 hours.

The catalysts were filtered off, the solvent was removed in vacuo and the residue was dissolved in dry ether. The product precipitated from the ethereal solution as a white powder (7.2 g) m.p. 124°–128°.

(b) 4-Hydroxy-$\alpha^1$-[[[1-methyl-3-(phenylamino)propyl]amino]methyl]-1,3-benzenedimethanol, dihydrochloride, hemihydrate 2-Hydroxy-5-[1-hydroxy-2-[[1-methyl-2-[(phenylamino)carbonyl]ethyl]amino]ethyl]benzoic acid, methyl ester (2.85 g) in tetrahydrofuran (30 ml) was added dropwise to lithium aluminium hydride (1.5 g) in tetrahydrofuran (150 ml) at 0° with stirring.

The stirred mixture was then heated at reflux for 8 hours and cooled. Water (7.5 ml) was added cautiously and 5 M hydrochloric acid (ca. 45 ml) was added until the suspension had dissolved to give two layers. The stirred mixture was adjusted to pH 9 with sodium bicarbonate and the suspension was filtered. The filtrate was evaporated in vacuo and the residue was partitioned between ethyl acetate and 8% sodium bicarbonate. The organic layer was dried (MgSO$_4$) and evaporated in vacuo. The residue was stirred with dry ether and the liquors were decanted from the residual gum, filtered and treated with ethereal hydrogen chloride. The product was isolated as a buff powder (1.1 g) m.p. 90°–95°.

EXAMPLE 5

$\alpha^1$-[[[2-(Ethylphenylamino)-1-methylethyl]amino]methyl]-4-hydroxy-1,3-benzenedimethanol, dihydrochloride, hydrate 4-Hydroxy-$\alpha^1$-[[bis(phenylmethyl)amino]methyl]-1,3-benzenedimethanol (6.9 g) in ethanol (250 ml) was hydrogenated at room temperature and atmospheric pressure over pre-reduced 10% palladium oxide on charcoal (1.0 g) and 5% platinum oxide on charcoal (1.0 g). Hydrogen uptake was complete in 17 hr. 1-(Ethylphenylamino)-2-propanone (2.44 g) and acetic acid (1.9 ml) in ethanol (60 ml) were added and the mixture was hydrogenated at 40° and atmospheric pressure. Hydrogen uptake was complete in 6 hr.

The catalysts were filtered off, the solvent was evaporated in vacuo and the residue was dissolved in water (150 ml). The solution was adjusted to pH 9 with sodium bicarbonate and extracted with ethyl acetate (3×100 ml). The combined extracts were dried (MgSO$_4$) and the solvent was evaporated in vacuo.

The crude product was purified by column chromatography on silica. Methanol:ethyl acetate (1:9) eluted a minor impurity and methanol:ethyl acetate (3:7) gave the product as a solid foam (3.12 g).

The free base was dissolved in ethyl acetate and treated with ethereal hydrogen chloride to give the product as a white powder (3.4 g) m.p. 88°–93° (softens 78°).

EXAMPLE 6

4-Hydroxy-$\alpha^1$-[[[2-[(4-methoxyphenyl)methylamino]-1-methylethyl] amino]methyl]-1,3-benzenedimethanol, sulphate(1:2)

A solution of 4-hydroxy-$\alpha^1$-[[bis(phenylmethyl)amino]methyl]-1,3-benzenedimethanol (5.5 g) in ethanol (250 ml) was hydrogenated at 40° and atmospheric pressure over prereduced 10% palladium oxide on charcoal (1.0 g) and 5% platinum oxide on charcoal (1.0 g). Hydrogen uptake was complete in 3 hr.

1-[(4-methoxyphenyl)methylamino]-2-propanone (2.66 g) and acetic acid (1.6 ml) in ethanol (60 ml) were added and the mixture was stirred under nitrogen at 40° for 15 min and then hydrogenated at 40° and atmospheric pressure. Hydrogen uptake was complete in 2 hr.

The catalysts were filtered off, the solvent was evaporated in vacuo and the residue was dissolved in water (150 ml). The solution was adjusted to pH 9 with sodium bicarbonate and extracted with ethyl acetate (3×100 ml). The combined extracts were dried (MgSO$_4$) and the solvent was evaporated in vacuo.

The crude product was purified by column chromatography on silica. Methanol:ethyl acetate (1:9) eluted a minor impurity and methanol:ethyl acetate (3:7) gave the product as a yellow oil. The product was dissolved in ethyl acetate and treated with ethereal sulphuric acid. The product was isolated as a white powder (4.95 g) m.p.>150° (dec.).

EXAMPLE 7

4-Hydroxy-α¹-[[[1-methyl-3-(methylphenylamino)-propyl]amino]methyl]-1,3-benzenedimethanol

(a)
1-[4-Hydroxy-3-(hydroxymethyl)phenyl]-2-[[1-methyl-3-(methylphenylamino)propyl](phenylmethyl)amino]ethanone A solution of 2-bromo-1-[4-hydroxy-3-(hydroxymethyl)phenyl]ethanone (9.1 g) and N-methyl-N-phenyl-N'-(phenylmethyl)-1,3-benzenediamine (16.6 g) in butanone (200 ml) was heated under reflux for 4 hours. The mixture was cooled at 0° and the amine hydrobromide was filtered off. The filtrate was evaporated and a solution of the residue in 2 N hydrochloric acid (200 ml) was extracted with ethyl acetate. The acidic solution was basified with solid sodium bicarbonate and then extracted with ethyl acetate. The solvents were evaporated to give a brown gum (10.7 g). The crude product in ethyl acetate was filtered through a column of silica (100 g) to yield a light brown gum (7.9 g).

(b)
4-Hydroxy-α¹-[[[1-methyl-3-(methylphenylamino)-propyl](phenylmethyl)amino]methyl]-1,3-benzenedimethanol A solution of sodium borohydride (10 g) in water (30 ml) and 2 N sodium hydroxide (10 ml) was added over 10 minutes to a stirred solution of 1-[4-hydroxy-3-(hydroxymethyl)phenyl]-2-[[1-methyl-3-(methylphenylamino)propyl](phenylmethyl)amino]ethanone (7.8 g) in ethanol (100 ml) at 60°. The reaction was kept at 60° for 0.5 hour. The cooled mixture was acidified with 2 N hydrochloric acid and the ethanol was evaporated. Water (150 ml) was added and the solution was extracted with ethyl acetate. The aqueous layer was separated and basified with solid sodium bicarbonate and again extracted with ethyl acetate to give an off-white solid (7.4 g) m.p. 125°.

(c)
4-Hydroxy-α¹-[[[1-methyl-3-(methylphenylamino)-propyl]amino]methyl]-1,3-benzenedimethanol A solution of 4-hydroxy-α¹-[[[1-methyl-3-(methylphenyl)amino)propyl](phenylmethyl)amino]methyl]-1,3-benzenedimethanol (2.1 g) in ethanol (100 ml) containing acetic acid (0.65 ml) was hydrogenated over pre-reduced 10% palladium oxide on charcoal (0.3 g) for 18 hours. The catalyst and the solvent were removed and a solution of the residue in water (70 ml) was extracted with ethyl acetate. The aqueous solution was basified with solid sodium bicarbonate and the basic solution was extracted with ethyl acetate to give a colourless gum (1.2 g). The gum (1 g) was crystallised from isopropyl acetate (4 ml) to give a white solid (0.45 g) m.p. 95°-98°. Recrystallisation from isopropyl acetate gave (0.27 g) m.p. 99°-101°. Found: C, 69.58; H, 8.1; N, 7.99 $C_{20}H_{28}N_2O_3$ requires C, 69.74; H, 8.19; N, 8.13%.

EXAMPLE 8

4-Hydroxy-α¹-[[[1-methyl-3-(methylphenylamino)-propyl]amino]methyl]-1,3-benzenedimethanol, dihydrochloride, hydrate 4-Hydroxy-α¹-[[bis(phenylmethyl)amino]methyl]-1,3-benzenedimethanol (4.0 g) and 4-(methylphenylamino)-2-butanone (1.95 g) in ethanol (250 ml) were hydrogenated at room temperature and atmospheric pressure over pre-reduced 10% palladium oxide on charcoal (1.0 g) and 5% platinum oxide on charcoal (1.0 g). Hydrogen uptake was complete in 24 hours.

The catalysts and solvent were removed and the residue was purified by column chromatography on silica gel. Ethyl acetate:methanol (7:3) eluted the product as a yellow oil which was converted into its hydrochloride salt in methanol.

The gummy product was triturated with ether to give a buff powder (0.9 g) which softened above 50°. Equivalent weight, Found 238; requires 218. Found: C, 55.1; H, 7.1; N, 6.2 $C_{20}H_{28}N_2O_3$ 2HCl.H₂O requires C, 55.2; H, 7.4; N, 6.4%.

EXAMPLE 9

α¹-[[[2-[N-(4-Fluorophenyl)-N-methylamino]-1-methylethyl]amino]methyl]-4-hydroxy-1,3-benzenedimethanol, hydrochloride (1:1.5)

4-Hydroxy-α¹-[[bis(phenylmethyl)amino]methyl]-1,3-benzenedimethanol (5.0 g) in ethanol (200 ml) was hydrogenated at room temperature and atmospheric pressure over pre-reduced 10% palladium oxide on charcoal (1.0 g) and 5% platinum oxide on charcoal (1.0 g). Hydrogen uptake was complete in 22 hours. Acetic acid (1.45 ml) was added and the stirred mixture was heated to 50° under nitrogen. 1-[N-(4-Fluorophenyl)-N-methylamino][-2-propanone](2.00 g) in ethanol (50 ml) was added and the stirred mixture was hydrogenated at 50° and atmospheric pressure. Hydrogen uptake was complete in 8 hours. The catalysts were filtered off, the solvent was evaporated in vacuo and the residue was dissolved in 8% sodium bicarbonate (200 ml) and extracted with ethyl acetate (3×150 ml). The combined extracts were dried (MgSO₄) and the solvent was evaporated in vacuo. The crude product was purified by column chromatography on silica. Ethyl acetate:methanol (3:1) eluted the product as a yellow oil. The product was dissolved in the minimum of cold ethyl acetate, diluted with ether (200 ml) and then treated with ethereal hydrogen chloride. The hydrochloride salt was isolated as a white powder (2.3 g) m.p. 88°-93°.

EXAMPLE 10

4-Hydroxy-α¹-[[[1-methyl-2-[N-methyl-N-(4-methylphenyl)amino]ethyl]amino]methyl]-1,3-benzenedimethanol, dihyrochloride 4-Hydroxy-α¹-[[bis(phenylmethyl)amino]methyl]-1,3-benzenedimethanol (5.0 g) and 1-[N-methyl-N-(4-methylphenyl)amino]-2-propanone (2.03 g) in ethanol (300 ml) were hydrogenated at room temperature and atmospheric pressure over pre-reduced 10% palladium oxide on charcoal (1.0 g) and 5% platinum oxide on charcoal (1.0 g). Hydrogen uptake was complete in 22 hours. The catalysts were filtered off, the solvent was evaporated in vacuo and the residue was purified by column chromatography on silica. Ethyl acetate:methanol (3:1) eluted the product as a yellow oil contaminated with silica. The product was dissolved in the minimum of cold ethyl acetate, diluted with ethyl acetate (200 ml) and treated with hydrogen chloride. The dihydrochloride salt was isolated as a cream powder (2.25 g) m.p. 50° (dec.).

In a similar manner 4-hydroxy-α¹-[[bis(phenylmethyl)amino]methyl]-1,3-benzenedimethanol was reductively alkylated with the appropriate ketone to give the following compounds of the invention:

4-Hydroxy-$\alpha^1$-[[[2-[(4-hydroxyphenyl)methylamino]-1-methylethyl]amino]methyl]-1,3-benzenedimethanol, m.p. 80° (dec.) from 1-[methyl-[4-(phenylmethoxy)-phenyl]amino]-2-propanone.

4-Hydroxy-$\alpha^1$-[[[1-methyl-2-[(2-methylphenyl)amino]ethyl]amino]methyl]-1,3-benzenedimethanol, dihydrochloride hemihydrate, m.p. 85° (dec.) from 1-[(2-methylphenyl)(phenylmethyl)amino]-2-propanone.

$\alpha^1$-[[[3-(Ethylphenylamino)-1-methylpropyl]amino]methyl]-4-hydroxy-1,3-benzenedimethanol, dihydrochloride, hemihydrate m.p. 70° (dec.) from 4-(ethylphenylamino)-2-butanone.

4-Hydroxy-$\alpha^1$-[[[1-methyl-3-[(2-methylphenyl)amino]propyl]amino]methyl]-1,3-benzenedimethanol, dihydrochloride m.p. 75° (dec.) from 4-[(2-methylphenyl)amino]-2-butanone.

$\alpha^1$-[[[2-(4-Fluorophenyl)methylamino-1-methylpropyl]amino]methyl]-4-hydroxy-1,3-benzenedimethanol, dihydrochloride, hydrate, m.p. 54°–57°, from 4-[(4-fluorophenyl)methylamino]-2-butanone.

4-Hydroxy-$\alpha^1$-[[[1-methyl-3-[methyl-(2-methylphenyl)-amino]propyl]amino]methyl]-1,3-benzenedimethanol, dihydrochloride, sesquihydrate, m.p. 90°–100°, from 4-[methyl-(2-methylphenyl)amino]-2-butanone.

4-Hydroxy-$\alpha^1$-[[[1-methyl-3-[methyl-[3,4-[methylenebis(oxy)]phenyl]amino]propyl]amino]methyl]-1,3-benzenedimethanol, m.p. 50° (dec.), from [methylenebis(oxy)benzeneamino]-2-butanone.

EXAMPLE 11

$\alpha^1$-[[[1,1-Dimethyl-2-(methylphenylamino)ethyl]amino]methyl]-4-hydroxy-1,3-benzenedimethanol (a) N-Methyl-N-phenyl-2-methyl-1,2-propanediamine Potassium cyanide (7.5 g) was added to concentrated sulphuric acid (25 ml) cooled in an ice-bath. 2-Methyl-3-(methylphenylamino)-2-propanol (4.7 g) was added and the mixture was stirred at room temperature for 24 hours. Water (25 ml) was added to the cooled reaction mixture and the solution was heated on a steam-bath for 2.5 hours, cooled in ice and basified using 5 N sodium hydroxide and extracted into ether (4×100 ml), dried and evaporated to an orange oil (1.8 g). The oil was distilled under reduced pressure at 100° and 3×10$^{-2}$ mm Hg to give the diamine (1.6 g).

(b)

$\alpha^1$-[[[1,1-Dimethyl-2-(methylphenylamino)ethyl]amino]methyl]-4-phenylmethoxy-1,3-benzenedimethanol 5-(Dichloroacetyl)-2-(phenylmethoxy)benzoic acid, methyl ester (2.47 g) was added to freshly cut sodium (0.38 g) in analar methanol (80 ml) and the solution was heated under reflux for 15 minutes. 0.5 N Hydrochloric acid (10 ml) was added and the solution was heated under reflux for 15 minutes. The methanol was removed under reduced pressure and the glyoxal was extracted into ether (2×25 ml), dried (magnesium sulphate) and the filtrate evaporated to a yellow oil. N-Methyl-N-phenyl-2-methyl-1,2-propanediamine (1.2 g) in ethanol (25 ml) was added to the glyoxal in ethanol (25 ml) and the solution was heated under reflux for 2 hours. The resulting orange solution was evaporated down to a viscous oil. A solution of the oil in dry tetrahydrofuran (40 ml) was added to a solution of lithium aluminium hydride (1 g) in dry tetrahydrofuran (20 ml) under nitrogen and cooled in ice. The mixture was stirred for 18 hours at room temperature.

The mixture was cooled in an ice-bath and water (1 ml) was added, followed by 2 N sodium hydroxide (2 ml) and water (3 ml) and the mixture was filtered. The filtrate was dried (magnesium sulphate) and evaporated to dryness to yield a yellow oil. The product was purified by column chromatography on silica, the eluent being ethyl acetate/methanol 95:5. $\alpha^1$-[[[1,1-Dimethyl-2-(methylphenylamino)ethyl]amino]methyl]-4-phenylmethoxy-1,3-benzenedimethanol was obtained as a colourless oil which gave a friable solid under high vacuum (1.4 g) m.p. 93°–98°.

(c)

$\alpha^1$-[[[1,1-Dimethyl-2-(methylphenylamino)ethyl]amino]methyl]-4-hydroxy-1,3-benzenedimethanol $\alpha^1$-[[[1,1-Dimethyl-2-(methylphenylamino)ethyl]amino]methyl]-4-phenylmethoxy-1,3-benzenedimethanol (1.3 g) in ethanol (60 ml) was hydrogenated over 10% palladium on charcoal (250 mg). The catalyst was filtered off and the filtrate was evaporated to an oil which foamed under high vacuum. The product crystallised as a white microcrystalline powder from dry ether (630 mg) m.p. 131°–133°.

EXAMPLE 12

4-Hydroxy-$\alpha^1$-[[[2-(methylphenylamino)ethyl]amino]methyl]-1,3-benzenedimethanol, hydrochloride (1:1.5), hydrate (a)

$\alpha^1$-[[[2-(Methylphenylamino)ethyl]amino]methyl]-4-(phenylmethoxy)-1,3-benzenedimethanol 5-(Dichloroacetyl)-2-(phenylmethoxy)benzoic acid, methyl ester (4.8 g) was added to sodium (0.68 g) in analar methanol (160 ml). The solution was heated under reflux for 10 minutes. 0.5 N Hydrochloric acid (20 ml) was added and the solution was heated under reflux for 15 minutes. The methanol was removed under reduced pressure and the glyoxal was extracted into ether (2×50 ml), dried (magnesium sulphate) and the filtrate was evaporated to a yellow oil.

N-Methyl-N-phenyl-1,2-ethanediamine (2.04 g) in ethanol (50 ml) was added to the glyoxal in ethanol (50 ml) and the solution was heated under reflux for 2 hours. The resultant red solution was evaporated down to a viscous red oil. A solution of the oil in dry tetrahydrofuran (80 ml) was added to a solution of lithium aluminium hydride (2 g) in dry tetrahydrofuran (50 ml) under nitrogen and cooled in ice. The mixture was stirred at room temperature overnight.

The mixture was cooled in an ice-bath. Water (2 ml) was cautiously added, followed by 2 N sodium hydroxide (4 ml) and water (6 ml), and the mixture was filtered. The filtrate was dried (magnesium sulphate) and evaporated to dryness yielding a yellow oil. The pure product was obtained by chromatography on silica, using ethyl acetate/methanol (9:1) as eluent. The oil obtained from the column gave an off-white solid on trituration under dry ether (1.2 g) m.p. 91°–94°.

(b)

4-Hydroxy-$\alpha^1$-[[[2-(methylphenylamino)ethyl]amino]methyl]-1,3-benzenedimethanol, hydrochloride (1:1.5), hydrate $\alpha^1$-[[[2-(Methylphenylamino)ethyl]amino]methyl]-4-(phenylmethoxy)-1,3-benzenedimethanol (0.9 g) in ethanol (100 ml) was hydrogenated over pre-reduced 10% palladium on charcoal (250 mg). The catalyst was filtered off and the filtrate was evaporated to dryness yielding a gum. The gum was dissolved in ethyl acetate and ethereal hydrogen chloride was added to the stirred solution. The product precipitated as a colourless solid (0.72 g) m.p. 90°–104°.

EXAMPLE 13

4-Hydroxy-$\alpha^1$-[[[1-methyl-4-(methylphenylamino)-butyl]amino]methyl]-1,3-benzenedimethanol, dihydrochloride (1:1.5), hydrate A solution of 4-hydroxy-$\alpha^1$-[[bis(phenylmethyl-)amino]methyl]-1,3-benzenedimethanol (1.22 g) and 5-(methylphenylamino)-2-pentanone (0.6 g) in ethanol (120 ml) was hydrogenated in the presence of 10% palladium on carbon (0.5 g) and 5% platinum on carbon (0.5 g) until uptake of hydrogen had ceased. The catalyst and solvent were removed and the residual oil chromatographed on silica (Merck 7734). Elution with ethyl acetate/methanol (9:1) gave the product as a gum. This gum was converted into the dihydrochloride salt sesquihydrate (0.63 g). This salt was a glass with no distinct melting point. Found: C, 55.3; H, 7.2; N, 5.6; $C_{21}H_{30}N_2O_3 \cdot 2HCl \cdot 1\frac{1}{2}H_2O$ requires C, 55.0; H, 7.7; N, 6.1%.

EXAMPLE 14

Pharmaceutical Compositions

| Tablets | per tablet |
|---|---|
| Active ingredient* (sieved through 60 mesh) | 2 mg |
| Spray dried calcium phosphate dihydrate | 176 mg |
| Sta-Rx 1500** | 20 mg |
| Magnesium Stearate | 2 mg |

**A free-flowing compressible form of starch. The powders are intimately mixed and compressed into tablets.

| Inhalation aerosols | dose in each can |
|---|---|
| Active ingredient* (Micronised) | 24 mg |
| Sorbitan trioleate | 2.4 mg |
| trichlorofluoromethane | 5.7 g |
| dichlorodifluoromethane | to 20.4 g |

A suspension of the finely powdered drug is dispersed in the trichlorofluoromethane containing the sorbitan trioleate. The required quantity of this suspension is metered into each can, a metering valve is crimped on to each can and the dichlorodifluoromethane is metered into each can by pressure-filling through the valve. The valve delivers 85 mg of total suspension in each metered dose, containing 100 μg of the drug.

| Inhalation capsules | per capsule |
|---|---|
| Active ingredient* (Micronised) | 200 μg |
| Lactose B.P. | 25 mg |

The drug and lactose are intimately mixed and the mix is filled into hard gelatin capsules. The capsules are used in a suitable insufflator which delivers a finely dispersed powder cloud to the patients lungs via the mouth.

| Injection solution | per 5 ml. ampoule |
|---|---|
| Active ingredient* | 0.50 mg |
| Hydrochloric Acid | q.s. to give pH 4.5 |
| Water for Injections BP | to 5.0 ml |

*The active ingredient is the compound prepared according to Example 1. This may be replaced by other compounds according to the invention, in particular that of Examples 7 and 8.

The solution is sterilised by membrane filtration and filled into sterilised ampoules.

We claim:

1. A compound of the formula

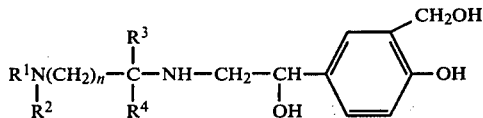

in which $R^1$ represents hydrogen or a straight or branched chain alkyl group;

$R^2$ represents a group of the formula

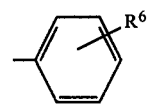

in which $R^6$ represents a hydrogen atom or independently at least one of a hydroxy, alkoxy, alkyl, halogen, dialkylamino or trifluoromethyl group;

$R^3$ and $R^4$ may independently represent hydrogen or a straight or branched chain alkyl group; and n represents 1, 2 or 3; or a pharmaceutically acceptable salt thereof; or a hydrate of said compound or salt thereof.

2. A compound as claimed in claim 1 in which $R^1$ represents hydrogen, methyl or ethyl.

3. A compound as claimed in claim 1 in which $R^3$ represents methyl and $R^4$ represents hydrogen or methyl.

4. A compound as claimed in claim 1 in which $R^6$ represents hydrogen, methoxy, fluorine, methyl or hydroxy.

5. A compound as claimed in claim 1 in which $R^1$ represents hydrogen, methyl or ethyl; $R^2$ represents phenyl, p-methoxyphenyl, p-fluorophenyl, o- or p-tolyl or p-hydroxyphenyl; $R^3$ represents hydrogen or methyl; and $R^4$ represents hydrogen or methyl.

6. A compound as claimed in claim 1 in which $R^1$ represents hydrogen, methyl or ethyl; $R^2$ represents phenyl or o- or p-tolyl; $R^3$ represents methyl; and $R^4$ represents hydrogen or methyl.

7. A compound as claimed in claim 1 which is 4-hydroxy-$\alpha^1$-[[[1-methyl-2-(methylphenylamino)ethyl]amino]ethyl]-1,3-benzenedimethanol.

8. A compound as claimed in claim 1 which is 4-hydroxy-$\alpha^1$-[[[1-methyl-2-(phenylamino)ethyl]amino]methyl]-1,3-benzenedimethanol, dihydrochloride.

9. A compound as claimed in claim 1 which is 4-hydroxy-$\alpha^1$-[[[1-methyl-3-(phenylamino)propyl]amino]methyl]-1,3-benzenedimethanol, dihydrochloride, hemihydrate.

10. A compound as claimed in claim 1 which is $\alpha^1$-[[[2-(ethylphenylamino)-1-methylethyl]amino]methyl]-4-hydroxy-1,3-benzenedimethanol, dihydrochloride, hydrate.

11. A compound as claimed in claim 1 which is 4-hydroxy-$\alpha^1$-[[[2-[N-(4-methoxyphenyl)-N-methylamino]-1-methylethyl]amino]methyl]-1,3-benzenedimethanol, sulphate.

12. A compound as claimed in claim 1 which is 4-hydroxy-$\alpha^1$-[[[1-methyl-3-(methylphenylamino)propyl]amino]methyl]-1,3-benzenedimethanol, or its dihydrochloride, hydrate.

13. A compound as claimed in claim 1 which is $\alpha^1$-[[[2-[N-(4-fluorophenyl)-N-methylamino]-1-methylethyl]amino]methyl]-4-hydroxy-1,3-benzenedimethanol, hydrochloride (1:1.5).

14. A compound as claimed in claim 1 which is 4-hydroxy-$\alpha^1$-[[[1-methyl-2-[N-methyl-N-(4-methylphenyl)amino]ethyl]amino]methyl]-1,3-benzenedimethanol, dihydrochloride.

15. A compound as claimed in claim 1 which is 4-hydroxy-$\alpha^1$-[[[2-[(4-hydroxyphenyl)methylamino]-1-methylethyl]amino]methyl]-1,3-benzenedimethanol.

16. A compound as claimed in claim 1 which is 4-hydroxy-$\alpha^1$-[[[1-methyl-2-[(2-methylphenyl)amino]ethyl]amino]methyl]-1,3-benzenedimethanol, dihydrochloride hemihydrate.

17. A compound as claimed in claim 1 which is $\alpha^1$-[[[3-(ethylphenylamino)-1-methylpropyl]amino]methyl]-4-hydroxy-1,3-benzenedimethanol, dihydrochloride, hemihydrate.

18. A compound as claimed in claim 1 which is 4-hydroxy-$\alpha^1$-[[[1-methyl-3-[(2-methylphenyl)amino]propyl]amino]methyl]-1,3-benzenedimethanol, dihydrochloride.

19. A compound as claimed in claim 1 which is $\alpha^1$-[[[2-(4-fluorophenyl)methylamino]-1-methylpropyl]amino]methyl]-4-hydroxy-1,3-benzenedimethanol, dihydrochloride, hydrate.

20. A compound as claimed in claim 1 which is 4-hydroxy-$\alpha^1$-[[[1-methyl-3-[methyl-(2-methylphenyl)amino]propyl]amino]methyl]-1,3-benzenedimethanol, dihydrochloride, sesquihydrate.

21. A compound as claimed in claim 1 which is $\alpha^1$-[[[1,1-dimethyl-2-(methylphenylamino)ethyl]amino]methyl]-4-hydroxy-1,3-benzenedimethanol.

22. A compound as claimed in claim 1 which is 4-hydroxy-$\alpha^1$-[[[2-(methylphenylamino)ethyl]amino]methyl]-1,3-benzenedimethanol, hydrochloride (1:1.5), hydrate.

23. A compound as claimed in claim 1 which is 4-hydroxy-$\alpha^1$-[[[1-methyl-4-(methylphenylamino)butyl]amino]methyl]-1,3-benzenedimethanol, dihydrochloride (1:1.5), hydrate.

* * * * *